United States Patent [19]
Eshel

[11] Patent Number: 5,257,977
[45] Date of Patent: Nov. 2, 1993

[54] TECHNIQUE FOR LOCALIZED THERMAL TREATMENT OF MAMMALS

[75] Inventor: Uzi Eshel, Herzlia, Israel
[73] Assignee: Argomed Ltd., Givataim, Israel
[21] Appl. No.: 669,366
[22] Filed: Mar. 14, 1991
[30] Foreign Application Priority Data
  Mar. 22, 1990 [IL] Israel ......................................... 93842
[51] Int. Cl.⁵ .................................................. A61F 7/12
[52] U.S. Cl. ...................................... 604/113; 604/96; 604/28; 607/105
[58] Field of Search .............................. 604/113–114, 604/43, 284, 96–97; 128/399–403; 606/27, 28

[56] References Cited

U.S. PATENT DOCUMENTS

| | | |
|---|---|---|
| 1,011,606 | 12/1911 | Fulton ................... 128/400 |
| 2,026,747 | 1/1936 | Nemzek ................ 128/400 |
| 2,466,042 | 4/1949 | Reich et al. .......... 128/401 |
| 2,849,001 | 8/1958 | Oddo . | 
| 3,227,154 | 1/1966 | Cook ..................... 128/401 |
| 4,244,377 | 1/1981 | Grams ................... 128/401 |
| 4,655,746 | 4/1987 | Daniels et al. . | |
| 5,007,437 | 4/1991 | Sterzer ................. 128/401 |

FOREIGN PATENT DOCUMENTS

| | | |
|---|---|---|
| 0105677 | 9/1983 | European Pat. Off. . |
| 0341988 | 11/1989 | European Pat. Off. . |
| 658662 | 10/1951 | United Kingdom . |
| 1563795 | 4/1980 | United Kingdom . |

Primary Examiner—C. Fred Rosenbaum
Assistant Examiner—Ronald Stright
Attorney, Agent, or Firm—Ladas & Parry

[57] ABSTRACT

A technique for localized thermal therapeutic treatment of mammals comprising the steps of inserting a catheter through a urethra, the catheter including a first elongate portion including first and second passageways for circulation of a heated fluid and a plurality of sealed elongate enclosures which contain trapped gas and provide thermal insulation surrounding the first and second passageways and a second portion void of insulation extending from the first elongate portion with extensions of the first and second passageways therethrough; and circulating a heated fluid through the first and second passageways to provide desired therapeutic heating of the body tissue surrounding the second portion by thermal dissipation from the surface thereof.

21 Claims, 5 Drawing Sheets

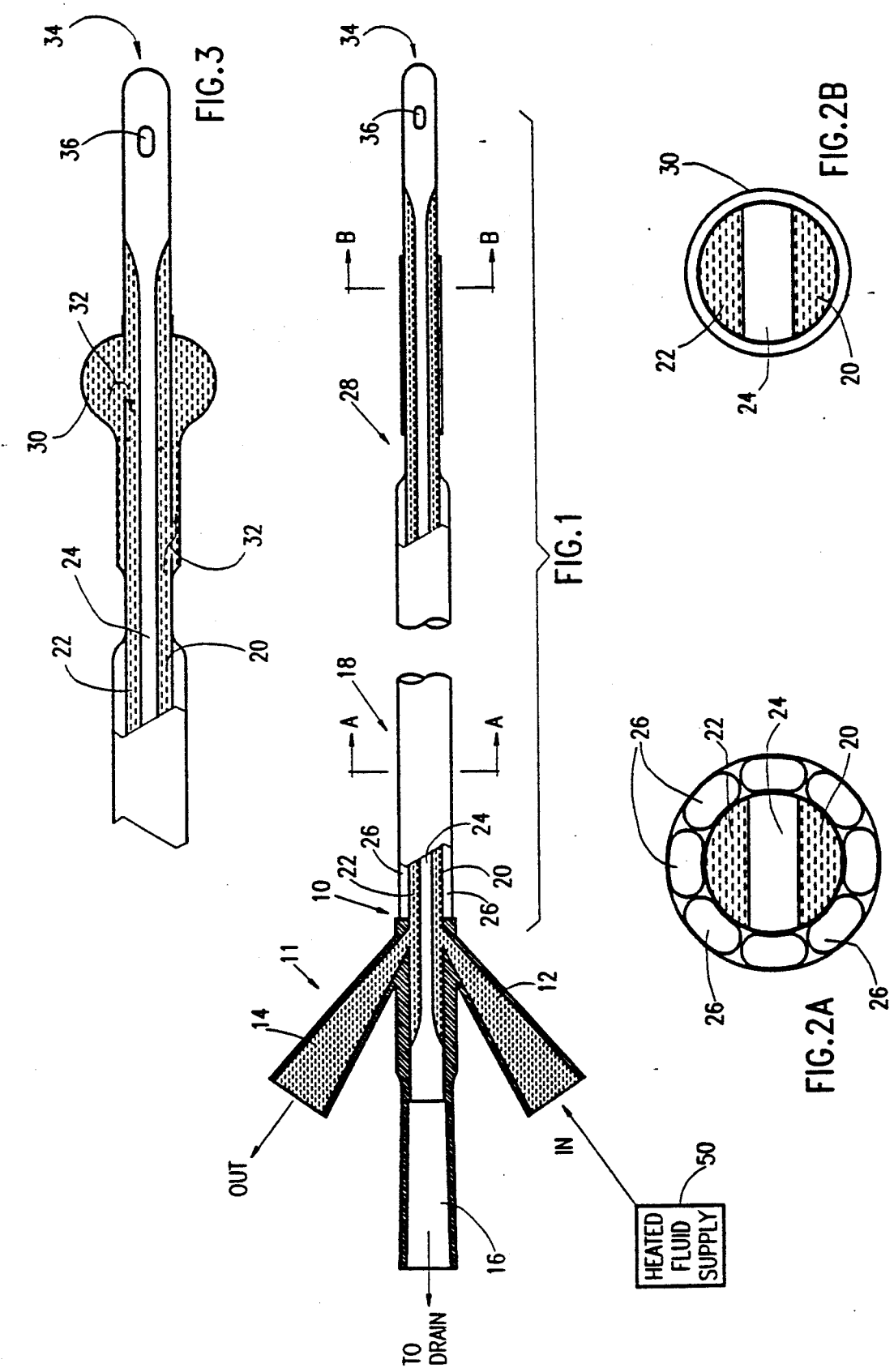

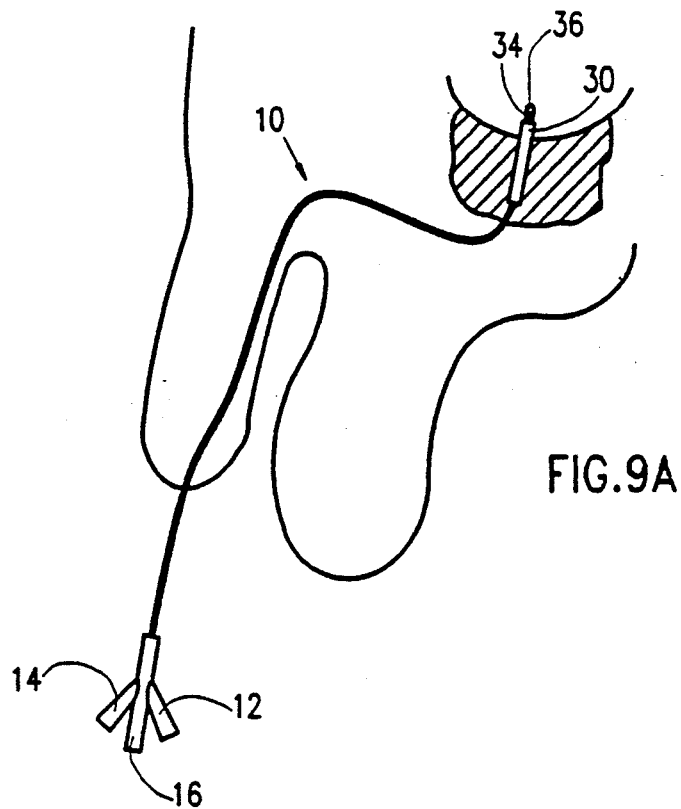
FIG.9A
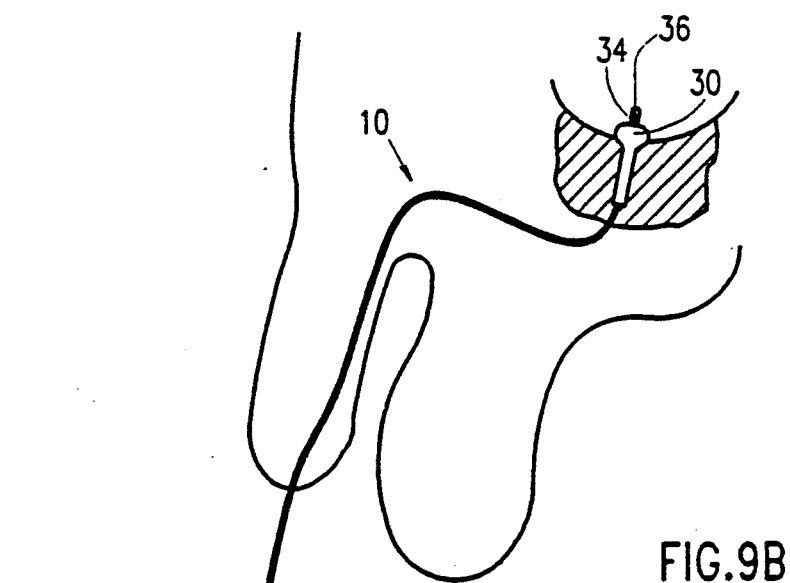
FIG.9B
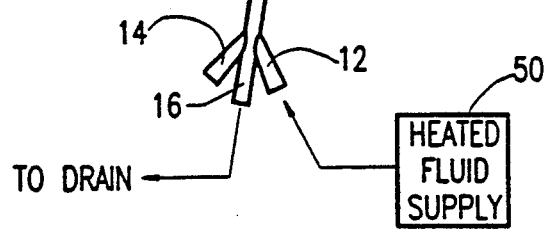

TECHNIQUE FOR LOCALIZED THERMAL TREATMENT OF MAMMALS

FIELD OF THE INVENTION

The present invention relates to a technique and apparatus for localized thermal treatment of mammals.

BACKGROUND OF THE INVENTION

There exist various medical conditions in humans which are alleviated by localized heat treatment. Examples include inflammations and malignancies in the bladder and prostate and urethral strictures.

Various techniques are known for dealing with the above mentioned problems. These include surgery and microwave heating as well as balloon expansion of passageways.

SUMMARY OF THE INVENTION

The present invention seeks to provide improved techniques and apparatus for localized thermal treatment of mammals.

There is thus provided in accordance with a preferred embodiment of the present invention a technique for localized thermal treatment of mammals comprising the steps of:

insertion through a body orifice a catheter including a first elongate portion including a first passageway for supply of a first heated fluid to a heating location and a second passageway for return of the first fluid from the heating location, thermal insulation surrounding the first and second passageways and a second elongate portion communicating with the first elongate portion and including extensions of the first and second elongate passageways in thermal contact with an exterior surface of the second elongate portion, such that the exterior surface is in heating contact with a desired interior body portion; and circulating of a heated fluid through the first passageway and the second passageway to provide desired heating of the desired interior body portion.

There is thus provided in accordance with a preferred embodiment of the invention a catheter including a first elongate portion including a first passageway for supply of a first heated fluid to a heating location and a second passageway for return of the first fluid from the heating location, thermal insulation surrounding the first and second passageways and a second elongate portion communicating with the first elongate portion and including extensions of the first and second elongate passageways in thermal contact with an exterior surface of the second elongate portion.

Further in accordance with a preferred embodiment of the present invention the second portion may be provided with a flexible and preferably expandable outer wall portion which is inflatable upon circulation of fluid through the first and second passageways. A catheter having such a second portion may be used to provide combination pressure and thermal treatment.

In accordance with another preferred embodiment of the invention, there is provided a technique for localized thermal and pressure treatment of enlarged prostate, diseased bladder or urethral strictures comprising the steps of:

insertion through the urethra a catheter including a first elongate portion including a first passageway for supply of a first heated fluid to a heating location and a second passageway for return of the first fluid from the heating location and a second elongate portion communicating with the first elongate portion and including a flexible, preferably expandable thermally transmissive wall the interior of which communicates with extensions of the first and second elongate passageways, such that the expandable wall portion is located at a location at which it is sought to apply pressure and heat; and circulating of a heated fluid through the first passageway and the second passageway under a suitable pressure to provide desired expansion of the wall portion of the second portion and thus desired heating and application of pressure at that location.

Additionally in accordance with a preferred embodiment of the present invention, there is provided a catheter including a first elongate portion including a first passageway for supply of a first heated fluid to a heating location and a second passageway for return of the first fluid from the heating location and a second elongate portion communicating with the first elongate portion and including a flexible and preferably expandable thermally transmissive wall the interior of which communicates with extensions of the first and second elongate passageways.

Additionally in accordance with another preferred embodiment of the invention, the catheter may also include a third elongate passageway extending through the first and second portions and having an opening for draining body fluids through the catheter. According to an alternative embodiment of the invention, the third elongate passageway may be used to accommodate a guide wire. This is particularly useful in treating urethral strictures.

The catheter may have a straight or curved tip, as suitable for a given use. The tip is typically defined beyond the second portion. Normally the opening communicating with the third elongate passageway may be located at any suitable location on the tip, such as, for example, axially at the end or at the side thereof.

BRIEF DESCRIPTION OF THE DRAWINGS

The present invention will be understood and appreciated more fully from the following detailed description, taken in conjunction with the drawings in which:

FIG. 1 is a partially sectional, partially side view illustration of a catheter constructed and operative in accordance with a preferred embodiment of the present invention in a non-inflated orientation;

FIGS. 2A and 2B are sectional illustrations taken along lines A—A and B—B respectively of FIG. 1;

FIG. 3 is a sectional illustration of a portion of the catheter of FIG. 1 in an inflated orientation;

FIGS. 9A and 9B illustrate initial placement and expansion of the catheter of FIG. 1 in prostate treatment;

DETAILED DESCRIPTION OF PREFERRED EMBODIMENTS

Figure 4B:
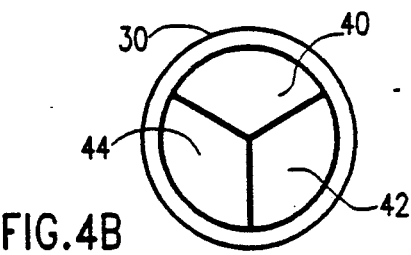
FIGS. 4A and 4B are sectional illustrations taken along lines A—A and B—B respectively of FIG. 1 in accordance with an alternative embodiment of the invention.

Reference is now made to FIGS. 1-3, which illustrate a preferred embodiment of the present invention. As seen in FIGS. 1-3, a catheter, indicated generally by reference numeral 10 is configured for insertion into a narrow body orifice, such as a urethra and is formed with an exterior portion. The exterior portion is indicated generally by reference numeral 11 and includes a heated fluid circulation inlet port 12, a heated fluid circulation outlet port 14 and a body fluid drain 16. The inlet and outlet ports 12 and 14 respectively may communicate with a heated fluid supply 50, such as a heating bath circulator commercially available from Haake Circulators of Haake Mess-Technik GmbH of Karlsruhe, W. Germany under catalog number D8-L.

The exterior portion communicates with and is normally integrally formed with a first insertable portion 18, typically having a length of 25-35 cm and having a cross section illustrated in FIG. 2A. The first portion 18 preferably defines a heated fluid inlet pathway 20, a heated fluid return pathway 22, a body fluid drain pathway 24 and a plurality of sealed elongate enclosures 26, which typically contain trapped air and act as a thermal insulator for the pathways 20 and 22. It is appreciated that pathways 20 and 22 are preferably surrounded by enclosures 26.

Communicating with the first portion 18 is a second portion 28, which is arranged to be located by suitable insertion of the catheter at a location requiring heat or heat and pressure treatment. The second portion 28 typically has a cross section illustrated in FIG. 2B and includes passageways 20, 22 and 24, as described above. Here, however, the insulating enclosures 26 are eliminated and are replaced by an flexible and preferably resilient and expandable wall portion 30, typically formed of latex, polyurethane, PVC or silicon rubber. The second portion is illustrated in FIG. 1 in an uninflated state and illustrated in FIG. 3 in an inflated state, the circulation of fluid from passageway 20 into the interior of wall portion 30 and therefrom to passageway 22 being indicated by arrows 32.

Figure 8A:
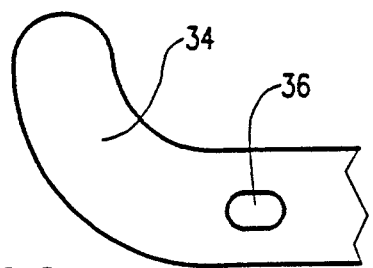
FIGS. 8A and 8B illustrate two alternative tip configurations useful in the catheter of FIG. 1.

The second portion 28 terminates in a tip portion 34 which is provided with an inlet aperture 36 for drainage thereinto of body fluids, such as urine. The tip portion 34 may have any suitable configuration. Two alternative conventional tip configurations are illustrated in FIGS. 8A and 8B.

Figure 8B:
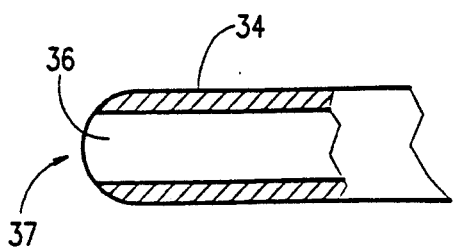

When the configuration of FIG. 8B is used, having an inlet aperture 36 disposed axially at the extreme end of the tip, body fluid drain passageway 24 may serve additionally or alternatively to accommodate a guide wire 37 for use in treatment of urethral strictures.

Figure 4A:
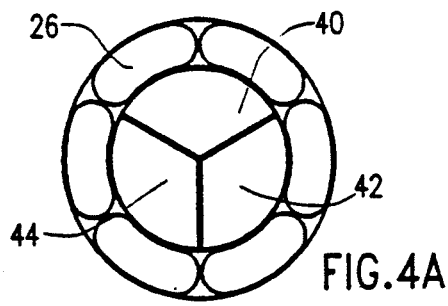

Reference is now made to FIGS. 4A and 4B, which illustrate two alternative cross-sectional configurations for the first and second portions of the catheter of FIG. 1. It is seen that in the embodiment of FIGS. 4A and 4B, the side by side orientation of passageway 20, 22 and 24, in the embodiment of FIGS. 2A and 2B is replaced by a radially divided configuration, defining passageways 40, 42 and 44 respectively.

Figure 5B:
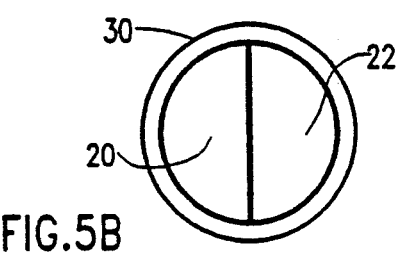
FIGS. 5A and 5B are sectional illustrations taken along lines A—A and B—B respectively of FIG. 1 in accordance with yet another alternative embodiment of the invention.
Figure 5A:
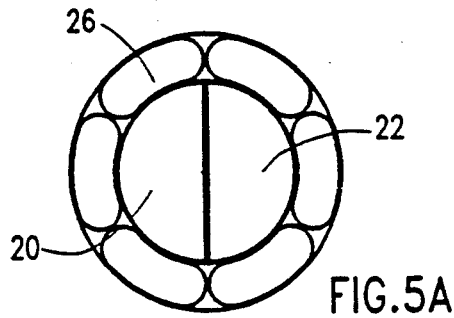

Reference is now made to FIGS. 5A and 5B, which illustrate two additional alternative cross-sectional configurations for the first and second portions of the catheter of FIG. 1. It is seen that in the embodiment of FIGS. 5A and 5B, passageway 24 is eliminated.

Figure 6B:
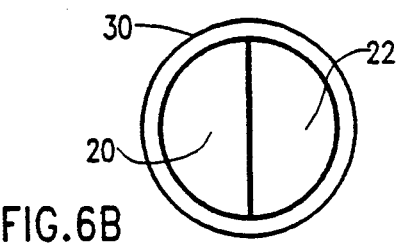
FIGS. 6A and 6B are sectional illustrations taken along lines A—A and B—B respectively of FIG. 1 in accordance with still another alternative embodiment of the invention.
Figure 6A:
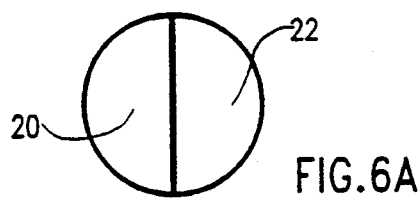

Reference is now made to FIGS. 6A and 6B, which illustrate two further alternative cross-sectional configurations for the first and second portions of the catheter of FIG. 1. It is seen that in the embodiment of FIGS. 6A and 6B, insulating enclosures 26 are eliminated and replaced by a relatively thick insulative wall, and passageway 24 is eliminated.

Figure 7B:
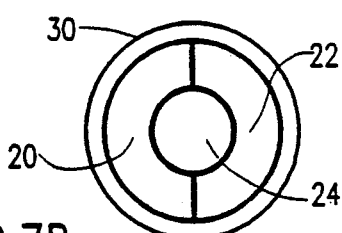
FIGS. 7A and 7B are sectional illustrations taken along lines A—A and B—B respectively of FIG. 1 in accordance with still a further alternative embodiment of the invention.
Figure 7A:
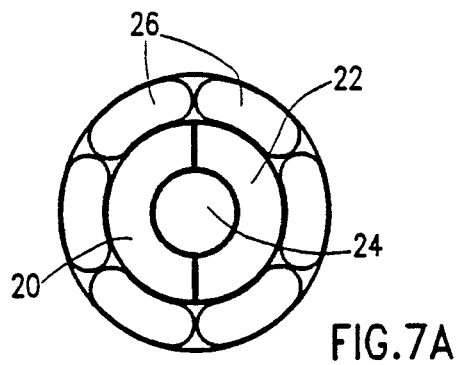

Reference is now made to FIGS. 7A and 7B, which illustrate two additional alternative cross-sectional configurations for the first and second portions of the catheter of FIG. 1. It is seen that in the embodiment of FIGS. 7A and 7B, passageway 24 is surrounded by passageways 20 and 22, each of which covers one half of the circumference of the cross section. Passageways 26 surround passageways 20 and 22 in the first portion of the catheter of FIG. 1.

Figure 10:
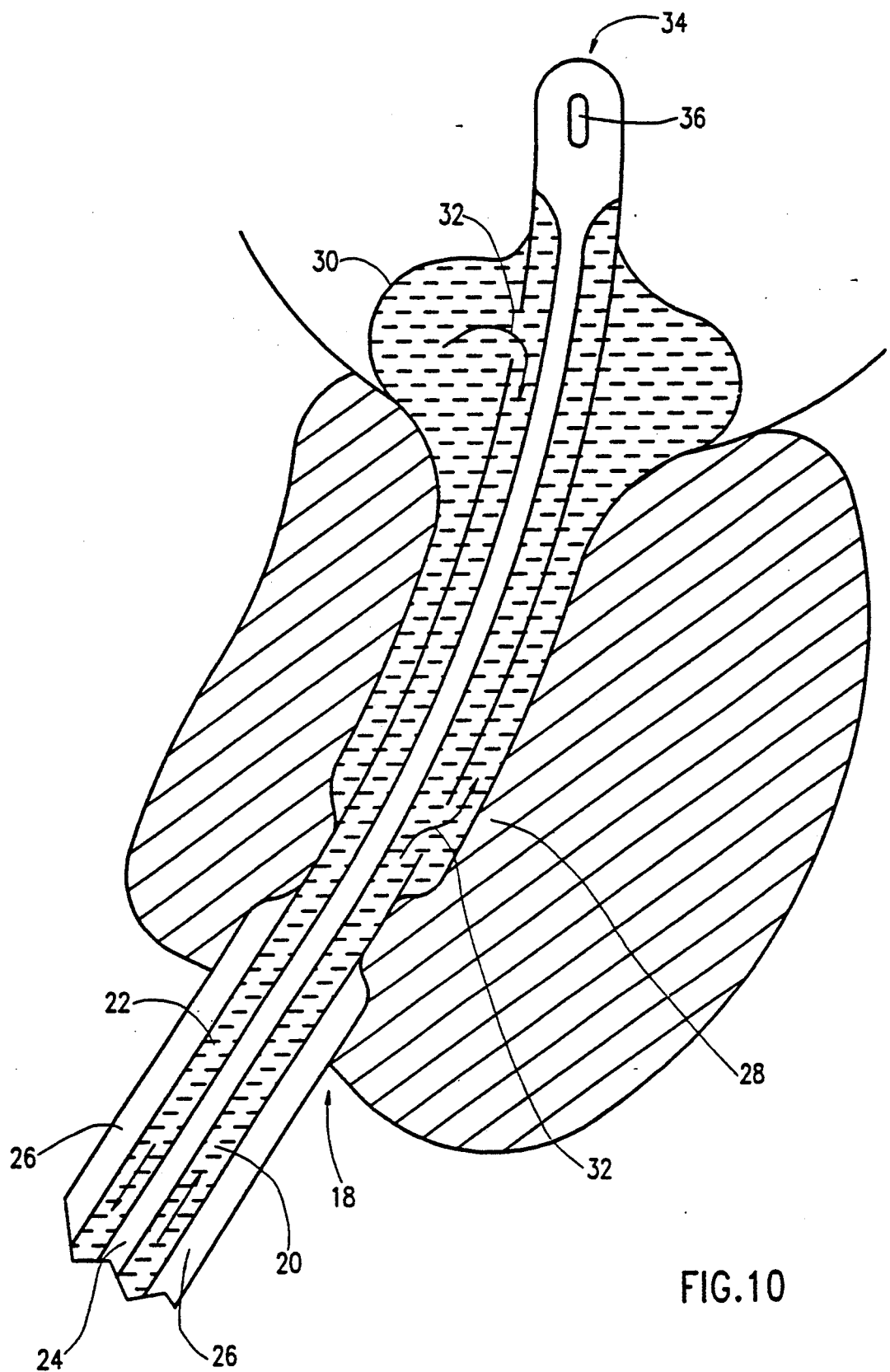
FIG. 10 illustrates in detail the second portion and tip of the catheter, when expanded, in prostate treatment.

Reference is now made to FIGS. 9A, 9B and 10, which illustrate use of the apparatus described hereinabove in the treatment of an enlarged prostate. FIG. 9A illustrates insertion of the catheter of FIGS. 1-3 through the urethra such that the second portion 28 lies at the top part of the prostate and extends into the bladder and the tip portion 34 extends into the bladder.

FIGS. 9B and 10 illustrate the supply of heated fluid under suitable pressure, typically 1-4 ATM from a heated fluid supply through the catheter 10 for inflation of the flexible wall portion 30 to the configuration illustrated. Such inflation provides heat or pressure and heat treatment to the prostate and the neck of the bladder, thus effectively enlarging the passageway of the urethra through the prostate, as desired. Drainage of urine from the bladder is provided via aperture 36.

In accordance with an embodiment of the invention, the catheter may be left in the patient after treatment to provide drainage of body fluids and to prevent inflammation of the treated area due to passage of urine in the vicinity thereof.

Figure 11A:
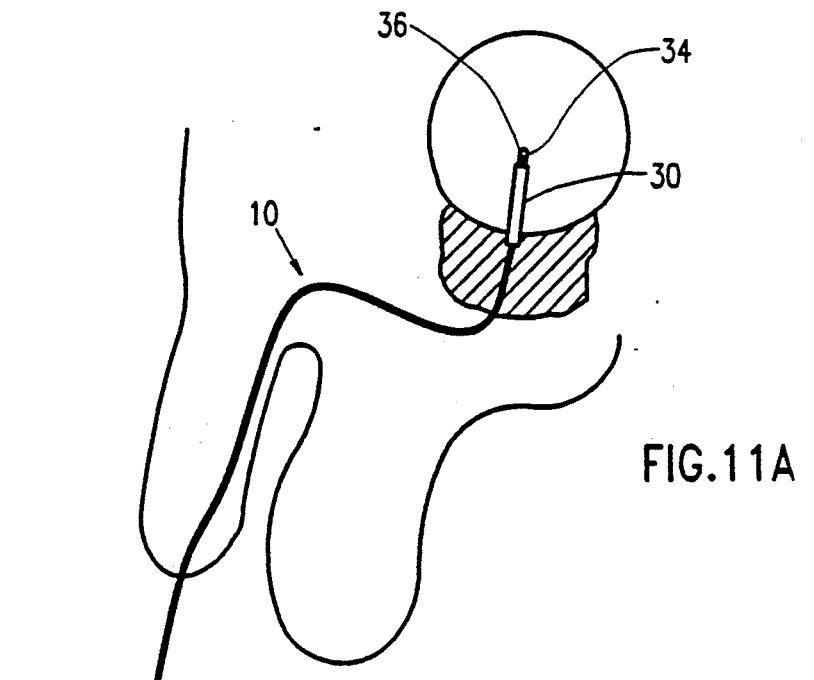
FIGS. 11A and 11B illustrate initial placement and expansion of the catheter of FIG. 1 in bladder treatment.
Figure 11B:
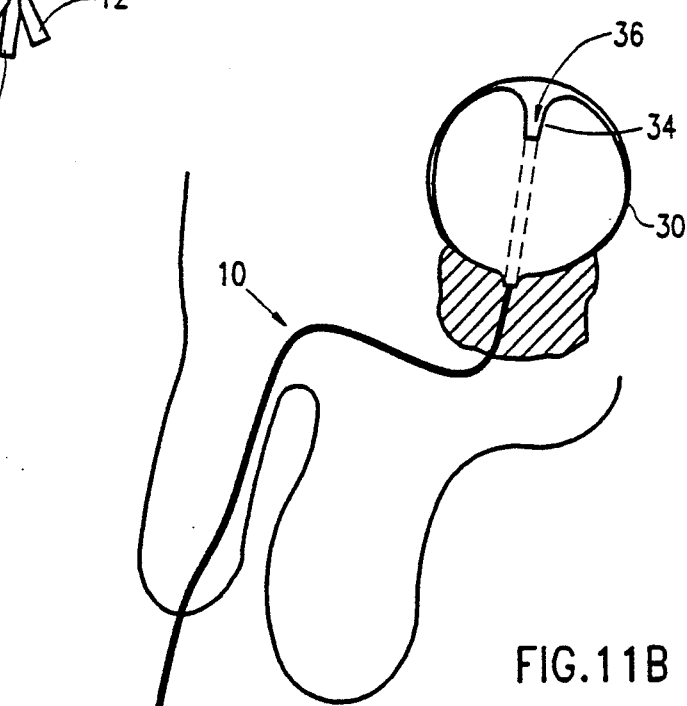

Reference is now made to FIGS. 11A and 11B, which illustrate thermal or combined thermal and pressure treatment of the bladder, in accordance with a present invention. In this case, the flexible wall portion 30 is configured to substantially fill the bladder. Normally the tip of the catheter is that shown in FIG. 8B.

Preferably the catheter of the present invention is made entirely of elastomeric materials and thus is suitable for use during and in combination with radiation therapy where suitable.

It will be appreciated by persons skilled in the art that the present invention is not limited by what has been particularly shown and described hereinabove. Rather the scope of the present invention is defined only by the claims which follow:

What is claimed is:

1. A catheter comprising:
   a first elongate portion including first and second passageways are in fluid communications with each other for circulation of a heated fluid and thermal insulation surrounding the first and second passageways, said thermal insulation comprising a plurality of sealed elongate enclosures which contain trapped gas; and a second elongate portion communicating with the first elongate portion and including extensions of the first and second elongate passageways therethrough and a flexible thermally transmissive wall the interior of which communicates with the extensions of the first and second elongate passageways.

2. A catheter according to claim 1 and also including a third elongate passageway extending through the first and second portions and having an inlet opening for draining body fluids through the catheter.

3. A catheter according to claim 2 and also comprising a tip portion extending from said second portion in which said inlet opening is defined.

4. A catheter according to claim 3 and wherein said tip portion is straight.

5. A catheter according to claim 1 and wherein said wall is inflatable upon circulation of a fluid under suitable pressure through the first and second passageways.

6. A catheter according to claim 1 and also including a third elongate passageway extending through the first and second portions and having an inlet opening accommodating a guide wire.

7. A catheter according to claim 3 and wherein said tip portion is curved.

8. A catheter comprising:
a first elongate portion including first and second passageways are in fluid communication with each other for circulation of a heated fluid; and
thermal insulation surrounding the first and second passageways, said thermal insulation comprising a plurality of sealed elongate enclosures which contain trapped gas; and
a second elongate portion communicating with the first elongate portion and including extensions of the first and second elongate passageways in thermal contact with an exterior surface of the second elongate portion.

9. A catheter according to claim 8 and also including a third elongate passageway extending through the first and second portions and having an inlet opening for draining body fluids through the catheter.

10. A catheter according to claim 8 and also including a third elongate passageway extending through the first and second portions and having an inlet opening accommodating a guide wire.

11. A technique for localized thermal therapeutic treatment of mammals comprising the steps of:
inserting through a urethra, a catheter including a first elongate portion including first and second passageways are in fluid communication with each other for circulation of a heated fluid and a plurality of sealed elongate enclosures which contain trapped gas and provide thermal insulation surrounding the first and second passageways and a second portion void of insulation extending from the first elongate portion with extensions of the first and second passageways therethrough; and
circulating a heated fluid through the first and second passageways to provide desired therapeutic heating of the body tissue surrounding the second portion by thermal dissipation from the surface thereof.

12. A technique according to claim 11 and wherein said catheter comprises a body fluid drainage passageway having inlet and outlet openings and extending alongside said first and second passageways and also including the step of draining body fluid through said body fluid drainage passageway during the treatment.

13. A technique according to claim 11 and wherein said catheter comprises a guide wire accommodating passageway having inlet and outlet openings and extending alongside said first and second passageways and also including the step of inserting said catheter along a guide wire.

14. A technique according to claim 11 and also comprising the step of retaining the catheter in the mammal after treatment.

15. A technique for localized thermal and pressure therapeutic treatment of a body portion comprising the steps of:
inserting through a urethra, a catheter including a first elongate portion including first and second passageways are in fluid communication with each other for circulation of a heated fluid and a plurality of sealed elongate enclosures which contain trapped gas and provide thermal insulation surrounding the first and second passageways and a second portion extending from the first elongate portion and including extensions of the first and second passageways therethrough and a flexible thermally transmissive wall void of insulation; and
circulating a heated fluid through the first and second passageways under a suitable pressure to provide desired expansion of the wall of the second portion thereby to achieve a desired therapeutic application of pressure to the body tissue surrounding the second portion and therapeutic heating of the body tissue surrounding the second portion by thermal dissipation from the surface thereof.

16. A technique according to claim 15 and wherein said catheter comprises a body fluid drainage passageway having inlet and outlet openings and extending alongside said first and second passageways and also including the step of draining body fluid through said body fluid drainage passageway during the treatment.

17. A technique according to claim 15 and wherein said catheter comprises a guide wire accommodating passageway having inlet and outlet openings and extending alongside said first and second passageways and also including the step of inserting said catheter along a guide wire.

18. A technique according to claim 15 and also comprising the step of retaining the catheter in the mammal after treatment.

19. A technique for localized therapeutic thermal and pressure treatment of prostate or bladder conditions or urethral strictures comprising the steps of:
inserting through a urethra, a catheter including a first elongate portion including first and second passageways are in fluid communications with each other for circulation of a heated fluid and thermal insulation surrounding the first and second passageways, said thermal insulation comprising a plurality of sealed elongate enclosures which contain trapped gas; and a second portion extending from the first elongate portion with extensions of the first and second passageways therethrough, wherein the extensions of the first and second passageways communicate with the interior of the exterior wall of the second portion which is void of insulation to allow thermal dissipation from the surface thereof to the surrounding body tissue; and circulating a heated fluid through the first and second passageways under a suitable pressure to provide desired expansion of the exterior wall of the second portion thereby to achieve a desired heating and application of pressure to the body tissue surrounding the second portion.

20. A technique according to claim 19 and wherein said catheter comprises a body fluid drainage passageway and also including the step of draining body fluid through said passageway during the heat and pressure treatment.

21. A technique according to claim 19 and wherein said catheter comprises a guide wire following passageway and also including the inserting the catheter along a guide wire.

* * * * *